US008815543B2

(12) United States Patent  
Kitamura et al.

(10) Patent No.: US 8,815,543 B2  
(45) Date of Patent: Aug. 26, 2014

(54) METHODS OF PRODUCING ANTIGEN-SPECIFIC B CELL POPULATIONS IN THE PRESENCE OF CD40:CD40L, BAFF:BAFF RECEPTOR AND FAS:FASL STIMULATION

(75) Inventors: Daisuke Kitamura, Tokyo (JP); Takuya Nojima, Chiba (JP)

(73) Assignee: Tokyo University of Science Educational Foundation Administrative Organization

( * ) Notice: Subject to any disclaimer, the term of this patent is extended or adjusted under 35 U.S.C. 154(b) by 0 days.

(21) Appl. No.: 13/504,111

(22) PCT Filed: Oct. 25, 2010

(86) PCT No.: PCT/JP2010/068868  
§ 371 (c)(1),  
(2), (4) Date: Apr. 25, 2012

(87) PCT Pub. No.: WO2011/052545  
PCT Pub. Date: May 5, 2011

(65) Prior Publication Data  
US 2012/0214192 A1    Aug. 23, 2012

(30) Foreign Application Priority Data  
Oct. 30, 2009    (JP) ................................ 2009-251362

(51) Int. Cl.  
*C12N 5/00* (2006.01)

(52) U.S. Cl.  
USPC ........................... 435/70.1; 435/325; 435/326

(58) Field of Classification Search  
None  
See application file for complete search history.

(56) References Cited

U.S. PATENT DOCUMENTS

| 5,817,516 | A | 10/1998 | Kehry et al. | |
|---|---|---|---|---|
| 2007/0172504 | A1 | 7/2007 | Shirwan et al. | |
| 2010/0248971 | A1* | 9/2010 | Inagaki et al. | 506/6 |
| 2011/0318758 | A1 | 12/2011 | Sutkowski et al. | |
| 2012/0045414 | A1* | 2/2012 | Delucia | 424/85.4 |
| 2012/0157662 | A1* | 6/2012 | Beaumont et al. | 530/387.1 |

FOREIGN PATENT DOCUMENTS

| JP | 7-528490 | 12/1997 |
|---|---|---|
| JP | 2009-251362 A | 10/2009 |
| WO | WO-2007/067681 A2 | 6/2007 |
| WO | WO-2009/020923 A1 | 2/2009 |

OTHER PUBLICATIONS

Attwood, Science 290: 471-473, 2000.*  
Skolnick et al., Trends in Biotech., 18(1):34 39, 2000.*  
Armitage et al., "Molecular and Biological Characterization of a Murine Ligand for CD40," *Nature*, 357:80-82 (1992).  
Hollenbaugh et al., "The Human T Cell Antigen gp39, a Member of the Tnf Gene Family, is a Ligand for the CD40 Receptor: Expression of a Soluble Form of gp39 with B Cell Co-Stimulatory Activity," *The EMBO Journal*, 11(12):4313-4321 (1992).  
Lam et al., "In Vivo Ablation of Surface Immunoglobulin on Mature B Cells by Inducible Gene Targeting Results in Rapid Cell Death," *Cell*, 90:1073-1083 (1997).  
Misawa et al., "A Method to Identify cDNAa Based on Localization of Green Fluorescent Protein Fusion Products," *PNAS*, 97(7):3062-3066 (2000).  
Moore et al., "BlyS: Member of the Tumor Necrosis Factor Family and B Lymphocyte Stimulator," *Science*, 285:260-263 (1999).  
Moriyama et al., "Rapid Up-Regulation of c-FLIP Expression by BCR Signaling Through the PI3K/Akt Pathway Inhibits Simultaneously Induced Fas-Mediated Apoptosis in Murine B Lymphocytes," *Immunology Letters*, 109:36-46 (2007).  
Mukhopadhyay et al., "Identification and Characterization of a Novel Cytokine, THANK, a TNF Homologue That Activates Apoptosis, Nuclear Factor-κb, and c-Jun $NH_2$-Terminal Kinase," *The Journal of Biological Chemistry*, 274(23):15978-15981 (1999).  
Muramatsu et al., "Specific Expression of Activation-Induced Cytidine Deaminase (AID), a Novel Member of the RNA-Editing Deaminase Family in Germinal Center B Cells," *The Journal of Biological Chemistry*, 274(26):18470-18476 (1999).  
Nojima et al., "Toward the Establishment of Germinal Center-Like B Cell Culture System," *Proceedings of the Japanese Society for Immunology*, 37:259 (1997). Abstract Only.  
Schneider et al., "BAFF, a Novel Ligand of the Tumor Necrosis Factor Family, Stimulates B Cell Growth," *J. Exp. Med.*, 189(11):1747-1756 (1999).  
Spriggs et al., "Recombinant Human CD40 Ligand Stimulates B Cell Proliferation and Immunoglobulin E Secretion," *J. Exp. Med.*, 176:1543-1550 (1992).  
Suda et al., "Molecular Cloning and Expression of the Fas Ligand, a Novel Member of the Tumor Necrosis Factor Family," *Cell*, 75:1169-1178 (1993).  
Takahashi et al., "Generalized Lymphoproliferative Disease in Mice, Caused by a Point Mutation in the Fas Ligand," *Cell*, 76:969-976 (1994).  
Takata et al., "Tyrosine Kinases Lyn and Syk Regulate B Cell Receptor-Coupled $Ca^{2+}$ Mobilization Through Distinct Pathways," *EMBO Journal*, 13(6):1341-1349 (1994).  
Viertlboeck et al., "The Chicken Leukocyte Receptor Complex Encodes a Primordial, Activating, High-Affinity IgY Fc Receptor," *PNAS*, 104(28):11718-11723 (2007).  
International Preliminary Report on Patentability for Application No. PCT/JP2010/068868, dated Jun. 12, 2012.  
International Search Report and Written Opinion for Application No. PCT/JP2010/068868, dated Jan. 6, 2011.

* cited by examiner

*Primary Examiner* — Phillip Gambel  
(74) *Attorney, Agent, or Firm* — Marshall, Gerstein & Borun LLP

(57) ABSTRACT

The present invention provides a method for producing an antigen-specific B cell population comprising IgG-positive B cells specific to a specific antigen, the method comprising: culturing IgG-positive B cells together with the specific antigen in the presence of IL-21, while conferring stimulation to the IgG-positive B cells via CD40, a BAFF receptor and Fas; and screening for antigen-specific B cells specific to the specific antigen to obtain an antigen-specific B cell population comprising the IgG-positive B cells specific to the specific antigen.

6 Claims, 5 Drawing Sheets

```
                              G
ATGGGATGGAGCTGTATCATCCTCTTCTTGGTAGCAACAGCTACAGGTAAGGGGCTCACAGTAGCAGGCTTGAGGTCTGGACATATATA

T
TGGGTGACAATGACATCCACTTTGCCTTTCTCTCCACAGGTGTCCACTCCCAGGTCCAACTGCAGCAGCCTGGGGCTGAGCTTGTGAAG

A    A                              T
CCTGGGGCTTCAGTGAAGCTGTCCTGCAAGGCTTCTGGCTACACCTTCACCAGCTACTGGATGCACTGGGTGAAGCAGAGGCCTGGACG

T
AGGCCTTGAGTGGATTGGAAGGATTGATCCTAATAGTGGTGGTACTAAGTACAATGAGAAGTTCAAGAGCAAGGCCACACTGACTGTAG

T              T                   A
ACAAACCCTCCAGCACAGCCTACATGCAGCTCAGCAGCCTGACATCTGAGGACTCTGCGGTCTATTATTGCGCAAGATACGATTACTAC
 C-
 A  AT
GGTAGTAGCTACTTTGACTACTGGGGCCAAGGCACCACTCTCACAGTCTCCTCA
```

Figure 6

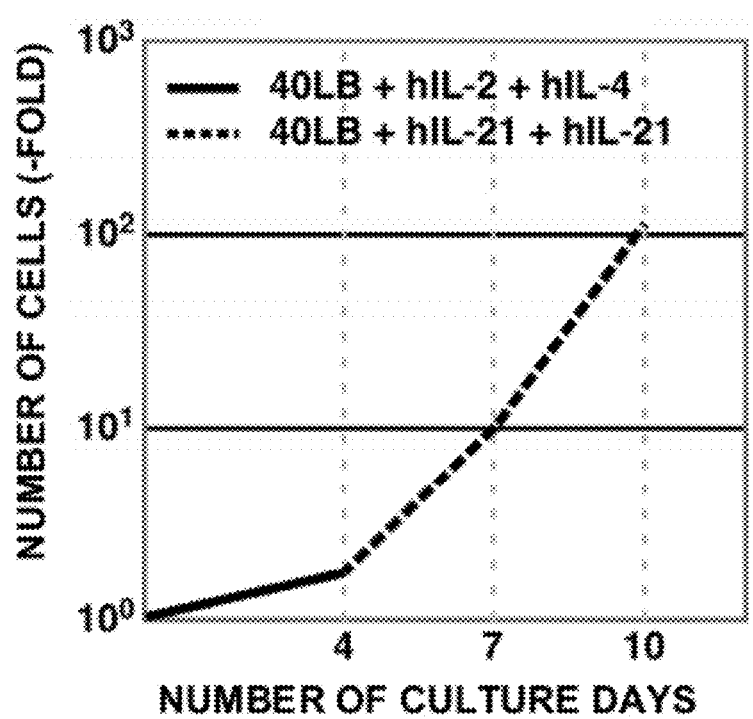

Figure 7

METHODS OF PRODUCING ANTIGEN-SPECIFIC B CELL POPULATIONS IN THE PRESENCE OF CD40:CD40L, BAFF:BAFF RECEPTOR AND FAS:FASL STIMULATION

TECHNICAL FIELD

The present invention relates to a method for producing an antigen-specific B cell population.

BACKGROUND ART

Monoclonal antibody, which exhibits high selectivity to a specific antigen, has attracted considerable attention as an effective drug in recent years. In particular, there are great expectations to develop an antibody drug that targets cancer cells. In order to apply a monoclonal antibody as an effective drug to the treatment of humans, administration of a human antibody having a small amount of heterogenetic antigen is most ideal from the viewpoint of prevention of immunological rejection. Thus, a large number of chimeric antibodies and humanized antibodies have been developed.

In general, a chimeric or humanized antibody used in the treatment of humans is produced by immunizing a mouse or the like with an antigen several times, then fusing a cell collected from the spleen or lymph node with a myeloma cell to form a hybridoma, and then applying a recombinant technique to a mouse IgG antibody produced by the hybridoma.

However, it takes a long period of time to treat individual animals and to select hybridomas that produce antibodies with high affinity. Moreover, it is necessary to confirm the activity of the antibody obtained by the recombinant technique. Thus, this method requires a long period of time to produce an antibody of interest, and further, the effects of the antibody cannot be confirmed until the antibody is administered to a human.

Furthermore, when an immunogen exhibits whole body toxicity, it is difficult to immunize an individual with it. Further, when a protein antigen which is highly conserved among animal species is used as an antigen, it is difficult to produce an antibody due to immunological tolerance.

On the other hand, it has been known that a B cell exhibiting high affinity for an antigen is selected in the germinal center. However, such selection mechanism has not yet been sufficiently elucidated. If it were possible to allow a B cell exhibiting high affinity for a specific antigen to artificially grow and to concentrate it, a monoclonal antibody exhibiting high affinity for a specific antigen could be produced in a shorter time.

As a method for allowing a B cell to grow, there has been known a method of culturing a B cell in the presence of a CD40 ligand (CD40L) and cytokine such as interleukin (IL)-4 (for example, National Publication of International Patent Application No. 9-512441 and J Exp Med. 1992 Vol. 176(6): pp. 1543-1550).

The germinal center is a histological structure formed as a result of the phenomenon that an antigen-non-contacted naive B cells is allowed to come into contact with an antigen and is thereby allowed to grow. It has been known that class switch and somatic hypermutation occurs in the B cells in the germinal center. For example, Abstract of the Annual Meeting of the Japanese Society for Immunology, 2007, Vol. 37, p. 259, 3-F-W41-16-O/P discloses that, when splenic B cells are cultured together with IL-4 and an anti-μHc antibody in the presence of fibroblasts in which BAFF and CD40L have been co-expressed, almost all of the B cells exhibit a germinal center-like phenotype, and approximately a half of the cells are class-switched to the IgG1, and that thereafter, if IL-4 is changed to IL-21, the number of IgE-positive cells increases.

SUMMARY OF INVENTION

Technical Problem

However, regardless of whether the B cells are naive B cells or antigen-contacted B cells, a technique of obtaining only B cells capable of producing an IgG antibody exhibiting high affinity for a specific antigen with high selectivity in a short time has not yet been developed.

Accordingly, it is an object of the present invention to provide a method for producing, in a simple manner, an antigen-specific B cell population comprising IgG-positive B cells specific to a specific antigen.

Solution to Problem

The present invention is as follows.

[1] A method for producing an antigen-specific B cell population comprising IgG-positive B cells specific to a specific antigen, the method comprising: culturing IgG-positive B cells together with the specific antigen in the presence of IL-21, while conferring stimulation to the IgG-positive B cells via CD40, a BAFF receptor and Fas on the IgG-positive B cells; and screening for antigen-specific B cells specific to the specific antigen to obtain an antigen-specific B cell population comprising the IgG-positive B cells specific to the specific antigen.

[2] The production method according to [1] above, wherein the stimulation via the CD40, the BAFF receptor and the Fas is conferred by CD40L, BAFF and FasL.

[3] The production method according to [1] or [2] above, wherein the IgG-positive B cells are obtained by performing a primary culture of a cell population comprising B cells in the presence of IL-4 and a secondary culture thereof in the presence of IL-21, while conferring stimulation to the IgG-positive B cells via CD40 and a BAFF receptor on the B cells.

[4] The production method according to any one of [1] to [3] above, wherein a carrier that presents the CD40L, the BAFF, the FasL and the specific antigen is used.

[5] The production method according to any one of [1] to [4] above, wherein a feeder cell that presents the CD40L, the BAFF, the FasL and the specific antigen is used.

[6] A method for producing a monoclonal antibody, comprising using the antigen-specific B cell population obtained by the production method according to any one of [1] to [5] to produce the monoclonal antibody.

[7] A feeder cell for use in screening for an antigen-specific B cell having CD40L, BAFF, FasL and a specific antigen on a surface thereof.

BRIEF DESCRIPTION OF THE DRAWINGS

FIG. 6 is a view showing the site of hypermutation of an antibody gene (SEQ ID NO: 3) in AID derivative cells of Example 4 of the present invention;

FIG. 7 is a graph of the growth curve of the human peripheral blood B cells of Example 5 of the present invention.

DESCRIPTION OF EMBODIMENTS

The method for producing an antigen-specific B cell population of the present invention is a method for producing an antigen-specific B cell population comprising IgG-positive B cells specific to a specific antigen, the method comprising: culturing the IgG-positive B cells together with the specific antigen in the presence of IL-21, while conferring stimulation to the IgG-positive B cells via CD40, a BAFF receptor and Fas on the IgG-positive B cells; and screening for the antigen-specific B cells specific to the specific antigen to obtain an antigen-specific B cell population comprising the IgG-positive B cells specific to the specific antigen (hereinafter these steps are referred to together as a "screening step").

Figure 1:
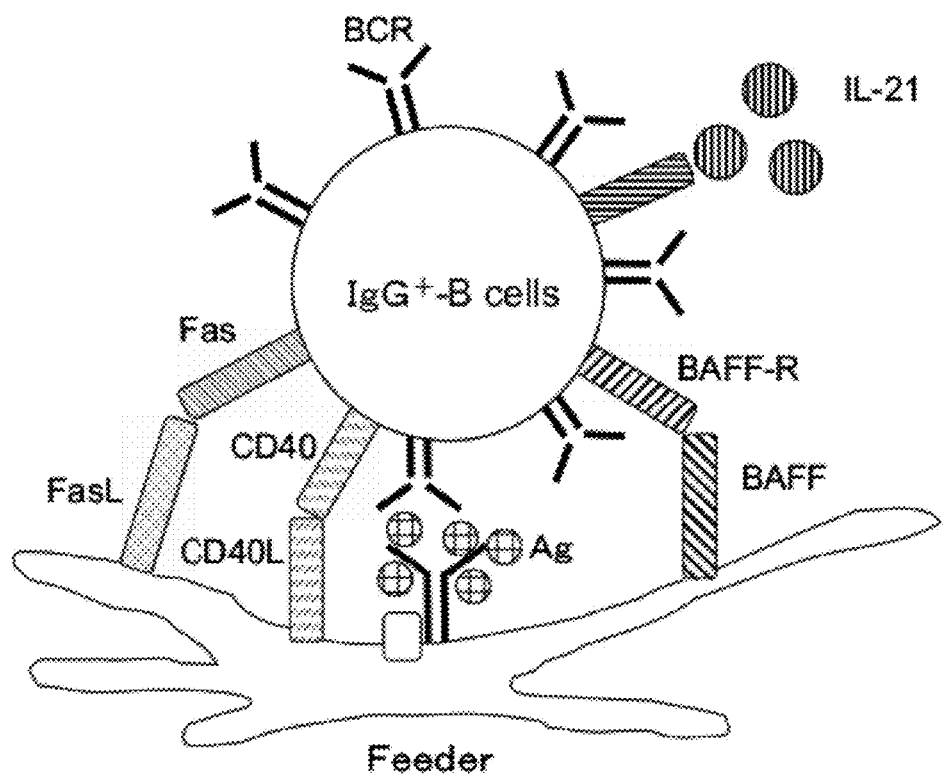
FIG. 1 is a conceptual view showing the screening for antigen-specific IgG-positive B cells according to the present invention, based on one embodiment in which feeder cells are used.

According to this method, IgG-positive B cells are cultured together with a specific antigen of interest in the presence of IL-21, while conferring stimulation to the IgG-positive B cells via CD40, a BAFF receptor and Fas on the IgG-positive B cells. Thus, instead of B cells having affinity for other antigens, IgG-positive B cells having affinity for the used specific antigen survive, so that other B cells are removed. Without wishing to be bound by any particular theory, it is assumed that an IL-21 receptor (IL-21 R), CD40, a BAFF receptor (BAFF-R) and Fas, as well as a B cell antigen receptor (BCR), are present on the surface of the IgG-positive B cell at this stage, and that among IgG-positive B cells stimulated via the CD40 and the BAFF-R, those other than IgG-positive B cells having a receptor for the used antigen (IgG-positive B cells having specificity to a specific antigen) die as a result of apoptosis induced by stimulation via the Fas (see FIG. 1). As a result, the cell population obtained after screening is an antigen-specific B cell population that is mainly constituted with IgG-positive B cells specific to the specific antigen.

Accordingly, an antigen-specific B cell population comprising IgG-positive B cells having specificity to a specific antigen can be simply and efficiently produced without having to perform immunization several times.

The term "step" is used in the present specification to include not only an independent step, but also a step that achieves the intended effect of the step, even in a case in which it cannot be clearly distinguished from other steps.

In addition, the numerical range represented by the symbol "-" (which means "to") is used in the present specification to mean that the numerical values described before and after the symbol "-" (which means "to") are included as the minimum and maximum values, respectively.

Moreover, in the present invention, in a case in which the amount of each ingredient in a composition is referred, if a plurality of substances corresponding to such ingredients exist in the composition, the aforementioned amount means the total amount of the plurality of substances existing in the composition, unless otherwise specified.

Hereinafter, the present invention will be described.

The IgG-positive B cells used in the present invention are B cells having IgG on the surface thereof. These IgG-positive B cells can be obtained from a cell population comprising B cells on the basis of the presence or absence of an IgG antibody.

The cell population comprising B cells used in the present invention are not particularly limited, as long as it may be generally derived from peripheral blood cells, bone marrow cells, or a lymphoid organ such as splenic cells. Moreover, the IgG-positive B cells may be either antigen-unreacted naive B cells, or B cells after being contacted with an antigen. The term "naive B cell" as used herein to generally mean a mature B cell that has not reacted with an antigen, and it corresponds to a cell that presents a surface antigen positive to CXCR5 and CD40.

Furthermore, the cell population used in the present invention is not particularly limited, as long as it comprises IgG-positive B cells, which have an IL-21 receptor (IL-21R), CD40, a BAFF receptor (BAFF-R) and Fas and are capable of recognizing an antigen. The cell population used in the present invention may also comprise B cells at other differentiation stages and various types of cells, unless they impede the purpose of the present invention. From the viewpoint of selection efficiency by culture, it is preferable to remove B cells other than IgG-positive B cells, such as IgE-positive cells and CD138-positive (plasma) cells, and cells other than the B cells, such as T cells, monocytes and NK cells.

The cell population used in the present invention may be a cell population derived from an organism whose immune system has been established. Examples of such an organism include mammals including: Primates such as a human and a monkey; Ungulata such as a swine, a bovine and a horse; rodents as small mammals such as a mouse, a rat and a rabbit; and Aves such as a chicken and a quail. The organisms, from which the present cell population is derived, are preferably a rodent and a primate, and examples of the organisms can include a mouse and a human. To the method of preparing a cell population from living tissues such as spleen, ordinary conditions for preparing a B cell population may be directly applied. Further, the present cell population is not limited to an organism-derived cell population, and an established B cell line may also be used.

To the culture of a cell population comprising IgG-positive B cells, generally, conventional culture conditions for a medium that is generally used in the culture of B cells may be applied. Examples of such a medium can include a Dalbecco's Modified Eagle's Medium (DMEM) and PRMI1640. To these media, generally, various types of additives applicable to ordinary cell culture, such as serum, various types of vitamins, and various types of antibiotics may be added.

As culture conditions such as culture temperature, conventional culture conditions used for B cells may be directly applied. Examples of such conditions include a culture at 37° C. in 5% $CO_2$.

The seeding density of a cell population in a medium depends on the origin of the cell population, the condition of cells prepared from tissues, and the number of culture days carried out in a single culture system. The seeding density may be set at generally $1 \times 10^2$ to $1 \times 10^7$ cells/cm$^2$, and preferably $1 \times 10^3$ to $1 \times 10^7$ cells/cm$^2$. In particular, in the case of human B cells, it is preferable to initiate the culture thereof at a high density in order to obtain a high growth rate. Thus, the seeding density of such human B cells may be preferably set at $1\times10^4$ to $1\times10^7$ cells/cm$^2$. If the seeding density is set within the aforementioned range, the cells can be prevented from reaching an excessive growth state after completion of the culture for approximately 4 days.

In order to generate intracellular signals from the IgG-positive B cells used in the present invention in the presence of IL-21 by giving stimulation to the IgG-positive B cells via CD40, a BAFF receptor and Fas, the IgG-positive B cells are required to have an IL-21 receptor (IL-21R), CD40, a BAFF receptor (BAFF-R) and Fas. The type of the stimulation given to these molecules is not limited, as long as it externally recognizes these molecules and generates intracellular signals inside the IgG-positive B cells having the CD40, the BAFF receptor and the Fas. Examples of such stimulation can include an antibody or an antibody fragment that recognizes all or a part of these molecules, a CD40 ligand (CD40L), BAFF and a Fas ligand (FasL). As such stimulation via CD40, a BAFF receptor and Fas, the present invention also includes an embodiment, in which stimulation is given using one or more of the CD40 ligand (CD40L), the BAFF and the Fas ligand (FasL), instead of using an antibody or an antibody fragment against CD40, a BAFF receptor (BAFF-R) or Fas.

CD40L is a ligand that binds to CD40, and the amino acid sequence of CD40L is publicly known (see, for example, Nature, Vol. 357, pp. 80-82 (1992), and EMBO J., Vol. 11, pp. 4313-4321 (1992)). The CD40L used in the present invention is not particularly limited, as long as it has a CD40L sequence that is conserved to such an extent that the binding ability of an active domain associated with the receptor-binding ability is not lost. For example, if certain CD40L has an active domain showing homology of 80% or more at the amino acid sequence level with that of the CD40L of the present invention, it can be used in the present invention. Such CD40L may be isolated from naturally expressing cells, or may be synthesized based on the known amino acid sequence. Moreover, the type of CD40L is not particularly limited, as long as it can give signals corresponding to the presence of the CD40L to B cells in a culture system. It may be either a free type or a membrane-bound type.

In order to form a cell population comprising IgG-positive B cells, the free-type CD40L may be present in a culture system in a concentration at which B cells can continuously grow. Thus, the concentration of the CD40L is set at 10 ng/ml to 10 µg/ml, for example. Taking into consideration a relative decrease associated with the growth of the B cells, the concentration of the CD40L can be preferably set at 100 ng/ml to 10 µg/ml.

It has been known that BAFF (B cell activation factor belonging to the tumor necrosis factor family) is a TNF-related molecule, which is associated with the growth, differentiation and the like of B cells that has reacted with an antigen. The amino acid sequence of BAFF has already been known (see, for example, J Exp Med, Vol. 189, pp. 1747-1756 (1999); Science, Vol. 285, pp. 260-263 (1999); and J Bio Chem, Vol. 274, pp. 15978-15981 (1999)). The BAFF used in the present invention is not particularly limited, as long as it has a BAFF sequence that is conserved to such an extent that the binding ability of an active domain associated with the receptor-binding ability is not lost. For example, if certain BAFF has an active domain showing homology of 80% or more at the amino acid sequence level with that of the BAFF of the present invention, it can be used in the present invention. Such BAFF may be isolated from naturally expressing cells, or may be synthesized based on the known amino acid sequence. Moreover, the type of BAFF is not particularly limited, as long as it can give signals corresponding to the presence of the BAFF to IgG-positive B cells in a culture system. It may be either a free type (namely, a secretory type) or a membrane-bound type.

In order to form a cell population comprising IgG-positive B cells, the free-type BAFF may be present in a culture system in a concentration at which B cells can continuously grow. Thus, the concentration of the BAFF is set at 10 ng/ml to 10 µg/ml, for example. The higher the concentration of the BAFF, the higher the cell survival-supporting activity that can be anticipated. From this viewpoint, the concentration of the BAFF can be preferably set at 100 ng/ml to 10 µg/ml.

Fas ligand (FasL) is a death factor belonging to a TNF family, namely a cytokine exhibiting an apoptosis-inducing activity. The amino acid sequence of the Fas ligand is publicly known (see, for example, Cell, Vol. 75, pp. 1169-1178 (1993)). The FasL used in the present invention is not particularly limited, as long as it has a FasL sequence that is conserved to such an extent that the binding ability of an active domain associated with the receptor-binding ability is not lost. For example, if certain FasL has an active domain showing homology of 80% or more at the amino acid sequence level with that of the FasL of the present invention, it can be used in the present invention. Such FasL may be isolated from naturally expressing cells, or may be synthesized based on the known amino acid sequence. Moreover, the type of FasL is not particularly limited, as long as it can give signals corresponding to the presence of the Fas to IgG-positive B cells in a culture system. Thus, the FasL may be either a free type or a membrane-bound type, as long as it can generate intracellular signals.

In general, the FasL may be present in a culture system in a concentration at which B cells can be induced to apoptosis. The concentration of the FasL is set at 10 ng/ml to 10 µg/ml, for example. From the viewpoint of induction of suppression of cell death by antigen stimulation, the concentration of the FasL can be preferably set at 10 ng/ml to 1 µg/ml.

As in the case of the above-mentioned cell population, examples of the origin of CD40L, BAFF and FasL include mammals such as Primates, Ungulata and rodents as small mammals, and Aves. Preferred examples of the origin include rodents and mammals, and specific examples can include a human and a mouse. Moreover, CD40L, BAFF and FasL may be derived from species, which is either identical to or different from the species of the above-mentioned cell population that would become a presentation target.

An antibody or an antibody fragment against CD40, a BAFF receptor (BAFF-R) or Fas can be obtained according to a method known in the art. The type of such an antibody or an antibody fragment is not particularly limited, as long as it has a binding ability to the CD40, the BAFF receptor (BAFF-R) or the Fas.

Such an antibody or an antibody fragment may be in the form of being presented on the surface of a carrier, or in a free-type or solubilized form in which it is not immobilized on the surface of the carrier.

From the viewpoint that intracellular signals are reliably given to a B cell in a culture system, CD40L, BAFF or FasL is preferably in the form of being presented on the surface of a carrier.

The type of a carrier used to present each molecule on the surface thereof is not particularly limited, as long as it is commonly used to present the molecule on the surface thereof. Examples of such a carrier can include a cell, an artificial lipid bilayer membrane, a plastic such as polystyrene or polyethylene terephthalate, collagen, nylon, nitrocellulose, agar, polysaccharide such as agarose or sepharose, a paper, and a glass. The shape of a carrier is not particularly limited.

It may adopt any shape such as a sheet, a plate, a sphere, a sponge or a fiber. From the viewpoint of reliable selectivity of cells, the carrier is preferably a cell. Examples of a cell that can be used as a carrier can include a fibroblast, an epithelial cell (e.g. HeLa cell), an embryonic kidney cell (e.g. HEK293, etc.), and a follicular dendritic cell. Of these cells, from the viewpoint of high growth rate, large cell surface area, and easy removal of feeder cells, fibroblasts are preferable.

A person skilled in the art can produce a feeder cell, on the surface of which CD40L, BAFF and FasL are presented, based on the known sequences of the CD40L, the BAFF and the FasL by applying a genetic recombination technique and the like.

As in the case of the above-mentioned cell population, examples of the origin of the feeder cell include mammals such as Primates, Ungulata and rodents as small mammals, and Aves. Preferred examples of the origin include rodents and mammals, and specific examples can include a mouse and a human. Moreover, the feeder cell may be derived from species, which is either identical to or different from the species of the above-mentioned cell population that would become a presentation target.

The specific antigen that is presented to IgG-positive B cells in the screening step means an antigen, for which antigen-specific IgG-positive B cells of interest exhibit affinity in the present invention. Such a specific antigen is appropriately selected depending on purpose. The type of the antigen is not particularly limited, as long as it exhibits antigenicity. Examples of the antigen can include a nucleic acid such as DNA or RNA, a sugar chain, a lipid, an amino acid, a peptide, a protein, a hapten, and a low molecular weight compound. These substances may be presented in a form, which can be recognized by B cells. The antigen may be either a free type or a carrier-immobilized type. From the viewpoint of reliable antigen presentation to B cells, the antigen is preferably immobilized on a carrier.

In order to enhance the antigen recognition ability of IgG-positive B cells, the antigen may be used alone or modified by techniques known in the art for enhancing antigenicity, such as addition of a known auxiliary molecule, and conjugation to an antibody molecule.

In the application of conjugation to an antibody molecule or fusion of a protein antigen with an antibody in the Fc region for antigen presentation, a scaffold for presenting an antigen on the surface of a carrier may be further used, such as an Fc receptor molecule, protein A, or protein G. Moreover, a fusion protein consisting of a protein that binds to a constitutional component of a carrier, and an antigenic protein, may also be used. Furthermore, in a case in which a membrane-type protein is presented as an antigen, the gene thereof may be incorporated into a vector, and the obtained expression vector may be then introduced into a cell used as a carrier, so that the gene may be expressed therein. In the case of proteins other than such a membrane-type protein, an expression vector capable of expressing an antigen in the form of a fusion protein consisting of a suitable signal peptide (which is not required in the case of a secretory protein) and a suitable transmembrane region (for example, the region of MHC class I) may be introduced into a cell used as a carrier, and the antigen may be then expressed therein.

From the viewpoint of the selection efficiency of antigen-specific B cells of interest, it is more preferable that CD40L, BAFF or FasL, and an antigen be presented on a feeder cell. It is to be noted that CD40L, BAFF, FasL and an antigen may not be necessarily present on a single feeder cell, as long as they can allow IgG-positive B cells to generate intracellular signals.

The IL-21 used in the screening step may be derived from the nature, or may be a recombinant IL-21 obtained by biological engineering. As in the case of the above-mentioned cell population, examples of the origin of the IL-21 include mammals such as Primates, Ungulata and rodents as small mammals, and Aves. Preferred examples of the origin of these molecules include rodents and mammals, and specific examples can include a mouse and a human. Moreover, the IL-21 may be derived from species, which is either identical to or different from the species of the above-mentioned cell population that would become a presentation target.

The amount of IL-21 contained in the culture system in the screening step is not particularly limited, as long as it is an amount at which IgG-positive B cells having affinity for a specific antigen can grow. In general, the amount of the IL-21 is set at preferably 1 ng/ml to 1 μg/ml, and more preferably 100 ng/ml to 1 μg/ml. In the screening step, from the viewpoint of the ratio of IgG-positive B cells in the obtained cell population, preferably, the culture system does not contain IL-4.

From the viewpoint of reliable screening, the period of time required for the screening step is generally half a day or longer after initiation of the screening step, although it depends on conditions such as seeding density and cell type. From the viewpoint of reliable screening, the period of time may be set at 1 to 3 days, and preferably 1 to 2 days. The period of time required for the screening step may also be longer, as long as the viability of cells is maintained. By culturing cells for a longer period of time, antigen-specific IgG-positive B cells having higher affinity for an antigen can be obtained.

In addition, in order to improve the affinity of B cells for an antigen, the screening step may be carried out repeatedly, while replacing feeder cells with fresh cells. In such a case, the after-mentioned secondary culture is preferably carried out after each screening step, in order to allow IgG-positive B cells to grow.

In order to improve the affinity of B cells for an antigen, the concentration and valence of the antigen may be changed (decreased) after repeating the step. Moreover, in order to improve the affinity of B cells for an antigen, the culture supernatant obtained immediately before a step, or an antibody generated in the culture supernatant may be added to a culture system, when the subsequent step is carried out. Thereby, competition occurs between the B cell receptor and the antibody, and a B cell having a B cell receptor with higher affinity can be screened for.

The IgG-positive B cell having an IL-21 receptor (IL-21 R), CD40, a BAFF receptor (BAFF-R) and Fas in the present invention may be obtained based on the reactivity with these molecules and the like, for example, when an antibody and the like are used. In view of a cell preparation time and the cell density of IgG-positive B cells of interest, the IgG-positive B cells are preferably obtained by a method comprising culturing a cell population comprising B cells by performing a primary culture step on the cell population in the presence of IL-4 and a secondary culture step thereon in the presence of IL-21, while conferring stimulation to the cell population via CD40 and a BAFF receptor (a culture step).

By carrying out such a two-stage culture process of using the different cytokines, IgG-positive B cells are allowed to grow in large quantities. By performing the present culture step, it becomes possible to increase IgG-positive B cells to a cell density of $10^3$ to $10^5$ of the initial density at the initiation of the culture, which depends upon seeding density at the initiation of the culture and the cell species.

In the above described culture step, both the primary culture and the secondary culture are carried out, while conferring stimulation to the cells via CD40 and a BAFF receptor. As in the screening step, such stimulation via CD40 and a BAFF receptor may be conferred using antibodies against these molecules, or CD40L and BAFF may also be used. Further, in view of surely conferring the stimulation from these antibodies and molecules to a cell population as a culture target, a carrier having these antibodies, or CD40L and BAFF, such as a feeder cell, may also be used. With regard to CD40L and BAFF, a carrier, etc., matters described in the screening step may be directly applied. The carrier or feeder cell used in the culture step may be referred to as a carrier for culture and a feeder cell for culture, respectively.

The IL-4 used in the primary culture may be derived from the nature, or may be a recombinant IL-4 obtained by biological engineering. From the viewpoint of effective growth of B cells, the concentration of IL-4 is preferably set at 1 ng/ml to 100 ng/ml. In addition, from the viewpoint of suppression of IgE cell propagation, the concentration of IL-4 is more preferably set at 1 ng/ml to 10 ng/ml.

Moreover, in the primary culture, depending on the type or origin of the B cell population used as a culture target, other cytokines may be used together with IL-4. For example, when IL-2 is used in combination with the IL-4, the concentration of the IL-2 is preferably set at 1 ng/ml to 1 μg/ml.

The seeding density of the cells applied upon initiation of the primary culture is not particularly limited. It depends on the origin of the cell population, the condition of cells prepared from tissues, and the number of culture days performed in a single culture system. In general, the seeding density may be set at $1 \times 10^2$ to $1 \times 10^6$ cell/cm$^2$, and preferably $1 \times 10^3$ to $1 \times 10^6$ cell/cm$^2$.

From the viewpoint of the growth rate of the B cell population, the period of time required for the primary culture may be generally set at 2 to 8 days after initiation of the culture, and from the viewpoint of the density of IgG-positive B cells in the cell population, the aforementioned period of time is set at preferably 3 to 6 days, and more preferably 3 to 5 days, although it may depend on the seeding density.

The secondary culture in the above described culture step is carried out in the presence of IL-21. The IL-21 may be derived from the nature, or may be a recombinant IL-21 obtained by biological engineering. From the viewpoint of effective growth of B cells, the concentration of IL-21 is set at preferably 1 ng/ml to 100 ng/ml, and more preferably 10 ng/ml to 100 ng/ml.

Although it depends on seeding density, from the viewpoint of the growth rate of the B cell population, the period of time required for the secondary culture may be generally set at 2 to 10 days after initiation of the secondary culture. Moreover, from the viewpoint of suppression of the number of plasmablasts in the cell population and an increase in the number of IgG-positive B cells, the aforementioned period of time is set at preferably 2 to 7 days, and more preferably 2 to 5 days. However, such a period of time may also be longer, as long as the viability of the cells can be maintained.

When the secondary culture is initiated, a predetermined amount of IL-21 may be added to the culture system after completion of the primary culture. Alternatively, cells may be recovered from the culture system after completion of the primary culture, and may be then transferred into an IL-21-containing medium that does not contain IL-4 to initiate the secondary culture. From the viewpoint of the growth rate of IgG-positive B cells in the secondary culture and suppression of the mingled IgE-positive B cells in the obtained cell population, it is most preferable to carry out the secondary culture in an IL-21-containing medium that does not contain IL-4.

As in the case of the above-mentioned cell population, examples of the origins of the IL-4 and IL-21 used in the present invention include mammals such as Primates, Ungulata and rodents as small mammals, and Aves. These molecules are preferably derived from rodents and mammals, respectively. Specific examples can include a mouse and a human. Moreover, the IL-4 and IL-21 may be derived from species, which is either identical to or different from the species of the above-mentioned cell population that would become a presentation target.

After completion of the secondary culture, in order to reliably enhance the concentration of B cells of interest, cells other than the IgG-positive B cells are preferably removed. Examples of cells to be removed can include IgE-positive B cells, CD138-positive plasma cells, and feeder cells (if they are present). These cells can be removed by a known technique using an antibody or the like against a specific surface antigen existing on the surface thereof.

Moreover, in the secondary culture, depending on the type or origin of the B cell population used as a culture target, other cytokines may be used together with IL-21. For example, when IL-2 is used in combination with the IL-21, the concentration of the IL-2 is preferably set at 1 ng/ml to 1 μg/ml.

In the method for producing an antigen-specific B cell population of the present invention, the screening for antigen-specific IgG-positive cells of interest may be carried out for a period of time necessary for the screening for the cells. The period of time necessary for the screening for the cells may be changed, as appropriate, depending on the number of IgG-positive B cells upon initiation of the screening step, the type of an antigen used, the condition of feeder cells, etc. For example, in order to efficiently obtain a cell population of interest, the screening step may be carried out for 1 to 2 days. When the production method comprises a culture step, the primary culture may be carried out for 3 to 5 days, the secondary culture may be then carried out for 2 to 5 days, and the section step may be then carried out for 1 to 2 days.

The production method of the present invention may comprise a growing step of allowing the screened antigen-specific IgG-positive B cells to further grow after the screening step. This growing step may be carried out under culture conditions capable of allowing antigen-specific IgG-positive B cells specific to a specific antigen, which have been screened in the screening step, to grow. From the viewpoint of the efficient growth of the screened IgG-positive B cells, the IgG-positive B cells are preferably cultured together with CD40L and BAFF in the presence of IL-21.

With regard to the IL-21 preferably used in the growing step, the conditions applied to the above described secondary culture or screening step can be directly applied. In addition, with regard to the CD40L and BAFF preferably used in the growing step as well, the above described matters can be directly applied.

The growing step may be continued for a period of time that is suitable for the number of IgG-positive B cells of interest in the obtained cell population. The period of time required for the growing step may be set at generally one or more days, and preferably three or more days. Such a period of time required for the growing step may be adjusted, as appropriate, depending on the growth rate of the cell population contained in the culture system or the cell density.

In the present invention, the term "antigen-specific IgG-positive B cell population" used for the cells obtained after the above described screening step is used to comprehensively mean the obtained cells as a whole, and thus, it is not limited by the number of cells. That is to say, this term includes not only a case in which a plurality of cells are present, but also a case in which only a single cell is present.

The antigen-specific IgG-positive B cell population of the present invention is a cell population obtained by the above described production method. This cell population is mainly constituted with IgG-positive B cells having specificity to a specific antigen used. For instance, the density of such IgG-positive B cells having specificity to an antigen is higher than that of a cell population from splenic tissues derived from a living body, which has been allowed to primarily come into contact with such an antigen.

Accordingly, the present antigen-specific IgG-positive B cell population can be preferably used in the production of a monoclonal antibody, which requires large quantities of IgG-positive B cells having affinity for a specific antigen, cell therapy, and the like.

With regard to B cells that constitute the IgG-positive B cell population obtained by the production method of the present invention, a mutation may be introduced into an antibody molecule, and B cells having a further variety of antigen specificities may be obtained. As an example of such mutation introduction, there is introduction of a mutation into a V region. Thereby, affinity for an antigen can be further improved.

As a method of introducing a mutation into a V region, a known method can be applied. From the viewpoint of reliable introduction of a mutation, there is applied AID (activation induced cytidine deaminase), which contributes to both of the somatic hypermutation (SHM) of an antibody gene and the class switch recombination of an antibody constant region gene. Alternatively, there may be used cytokine or the like, which reinforces the expression of AID.

The method for producing a monoclonal antibody of the present invention comprises using the cell population obtained by the above described method for producing an antigen-specific B cell population to produced the monoclonal antibody.

By this method, a monoclonal antibody against a specific antigen can be simply and rapidly obtained.

In the present method for producing a monoclonal antibody, a publicly known method for producing a hybridoma may be applied to the above described antigen-specific B cell population. Specifically, myeloma cells or the like are fused with the cell population comprising IgG-positive B cells obtained by the present invention according to a publicly known cell fusion method, so as to obtain hybridomas. From these hybridomas, hybridomas that produce antibodies of interest are isolated using a limiting dilution method or the like. Thereafter, antibodies produced by the isolated hybridomas may be recovered. Alternatively, there may also be applied a method, which comprises isolating antibody genes from the above described antigen-specific B cell population and then producing monoclonal antibodies by genetic recombination.

The feeder cells for use in screening for the antigen-specific B cells of the present invention have CD40L, BAFF, FasL and a specific antigen on a surface thereof.

Using the present feeder cells, the antigen-specific B cell population of the present invention can be efficiently obtained.

The present feeder cells for use in screening for the antigen-specific B cells of the present invention may present CD40L, BAFF, FasL and a specific antigen on the surface thereof, such that they can be recognized by B cells as presentation targets. An example of means for presenting these molecules on the cell surface includes introducing such a molecule into a target feeder cell, utilizing a genetic recombination technique or the like, such that it can be directly expressed in the form of a membrane-type naturally occurring molecule, or such that it can be expressed in the form of a fusion protein consisting of the aforementioned molecule and an anchor molecule that binds to the membrane.

The type of such a feeder cell is not particularly limited, as long as it is generally used in this purpose. Examples of feeder cells can include fibroblasts, epithelial cells (e.g. HeLa cells), embryonic kidney cells (e.g. HEK293, etc.), and follicular dendritic cells. Of these cells, from the viewpoint of high growth rate, large cell surface area, and easy removal of feeder cells, fibroblasts are preferable.

As in the case of the above-mentioned cell population and the like, examples of the origin of the feeder cell used in the present invention include mammals such as Primates, Ungulata and rodents as small mammals, and Aves. Preferred examples of the origins of these molecules include rodents and mammals, and specific examples can include a mouse and a human. Moreover, the feeder cell may be derived from species, which is either identical to or different from the species of the above-mentioned cell population that would become a presentation target.

In order to obtain the above described feeder cells for use in screening for antigen-specific B cells, there may also be used feeder cells for antigen presentation, which have only CD40L, BAFF and FasL, and do not have a specific antigen. In order to obtain feeder cells for use in screening for antigen-specific B cells, using the aforementioned feeder cells for antigen presentation, which have only CD40L, BAFF and FasL, means for presenting a specific antigen as a target on the cell surface is applied, for example, a specific antigen expression vector or the like may be used to allow feeder cells for antigen presentation to present a specific antigen, afterwards. Using such feeder cells for antigen presentation, feeder cells for use in screening for antigen-specific B cells having a specific antigen can be obtained depending on purpose, more efficiently than in the case of simultaneous introduction of all molecules.

EXAMPLES

The present invention will be described in the following examples. However, these examples are not intended to limit the scope of the present invention. It is to be noted that the symbol "%" used in the examples means weight (mass) %, unless otherwise specified.

Example 1

[A] Growth of IgG-Positive B Cells (1) Culture of Cells

The culture of a B cell preparation product and other cells was carried out using, as a B cell culture medium, RPMI-1640 (which contained 10% (v/v) FCS, penicillin/streptomycin, 2 mM L-glutamine, 55 nM 2-ME, 10 mM HEPES and 1 mM sodium pyruvate) under conditions of 5% (v/v) $CO_2$ and 37° C., unless otherwise specified.

(2) Preparation of Naive B Cells

Splenic cells were collected from a mouse (C57BL/6, female, 8-week-old). According to an ordinary method, a biotin-anti-mouse CD43 antibody (manufactured by BD Pharmingen), a biotin-anti-mouse CD4 antibody (manufactured by Biolegend), a biotin-anti-mouse Ter-119 antibody (manufactured by eBioscience), and a biotin-anti-mouse CD11c antibody (manufactured by eBioscience) were reacted with the cells. Thereafter, B cells that were negative to CD43, CD4, Ter-119 and CD11c were recovered using Streptavidin-Particle Plus-DM, BD IMAGNET™ (manufactured by BD Bioscience Pharmingen), and the recovered cells were then suspended in the above described culture medium, so as to obtain a B cell preparation product.

Feeder cells presenting CD40L and BAFF on the surface thereof, 40 LB cells, were obtained as follows. That is to say, a mouse CD40 ligand (see, for example, Nature, Vol. 357, pp. 80-82 (1992) and EMBO J., Vol. 11, pp. 4313-4321 (1992)) was incorporated into pApuro (EMBO J. 13: 1341-1349, 1994), so as to construct a CD40L expression vector. On the other hand, BAFF (see, for example, J. Exp Med, Vol. 189, pp. 1747-1756 (1999), Science, Vol. 285, pp. 260-263 (1999), and J Bio Chem, Vol. 274, pp. 15978-15981, (1999)) was incorporated into a vector composed of a promoter portion (from SnaBI to EcoRI) of pCAGGS (Gene 108: 193-199, 1991) and pEGFP-C1 (Clontech) (a portion comprising a neomycin resistance gene from BamHI to SnaBI), so as to construct a BAFF expression vector. These expression vectors were introduced into Balb/c 3T3 cells according to an ordinary method, and CD40 and BAFF were allowed to constantly express therein, thereby producing clones.

For this experiment, 40LB cells were plated at a cell density of $3 \times 10^6$ cells on a cell culture plate (manufactured by BD Falcon) having a diameter of 10 cm, and the cells were then cultured for 24 hours, so as to form a single layer. Thereafter, it was irradiated with 120 Gy of γ ray and it was then used.

(3) Preparation of IgG-Positive B Cell Population (Culture Step)

The above obtained mouse B cells were suspended at a cell density of $1.25 \times 10^4$ cells/ml in a B cell culture medium that contained mouse IL-4 (10 ng/ml, manufactured by PEPRO TECH), and the suspension was then cultured on 40LB in a $CO_2$ incubator (primary culture).

On Day 4 of the culture, the cells as a whole were peeled together with the feeder, using PBS containing 2 mM EDTA and 0.5% BSA, and the cells were then recovered by flushing with a pipette. The recovered cell population was plated at a cell density of $2.5 \times 10^3$ cells/ml or less on a B cell culture medium containing IL-21 (10 ng/ml, manufactured by PEPRO TECH) on a plate, on which newly prepared 40LB cells had been plated, followed by culture (secondary culture).

Figure 2:
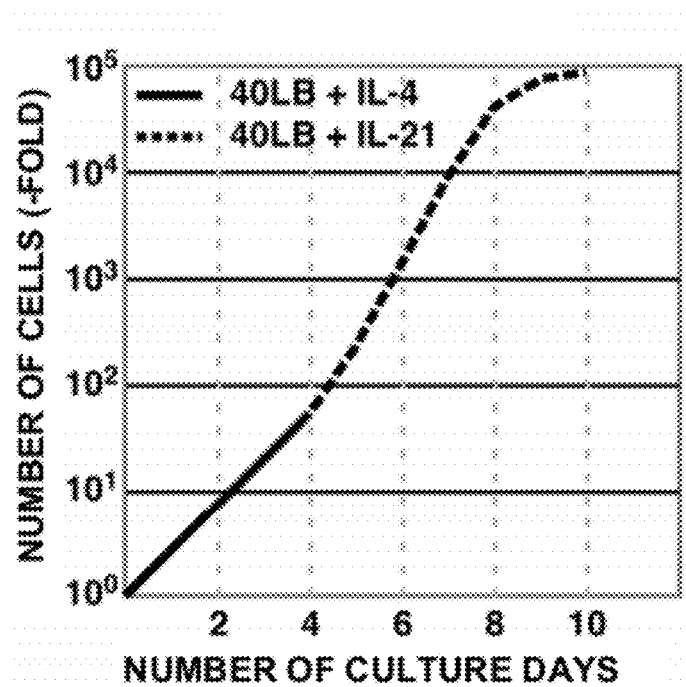
FIG. 2 is a graph of the growth curve of the B cells of Example 1 of the present invention.

On Days 4, 6, 8, and 10 after initiation of the culture, the number of living cells was counted by staining with trypan blue, and the increase rate of cells, which was calculated based on the initial number of cells, was obtained. The results are shown in FIG. 2. In FIG. 2, the solid line indicates the number of cells confirmed during the primary culture, and the dotted line indicates the number of cells confirmed during the secondary culture. As a result, it was confirmed that the cells had grown at a factor of approximately 100,000 for 10 days after initiation of the culture (see FIG. 2).

Figure 3:
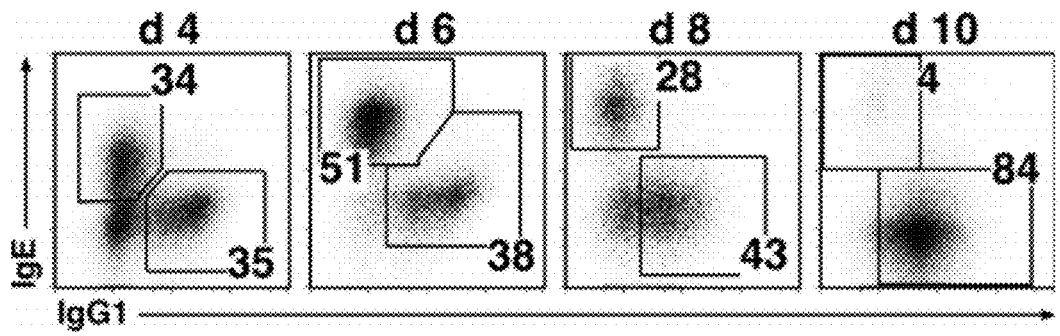
FIG. 3 is a view showing the results of the two-dimensional staining of the cell population during the primary and secondary cultures with an anti-IgE antibody and an anti-IgG1 antibody, performed in Example 1 of the present invention.

The B cells on Days 4, 6, 8 and 10 after initiation of the culture were stained with antibodies against IgE and IgG1, a biotin-anti-mouse IgE antibody (manufactured by BD Pharmingen) and an FITC-anti-mouse IgG1 antibody (manufactured by SouthernBiotec), for 20 minutes at a room temperature. Thereafter, the cells were analyzed with a flow cytometer FACS CALIBUR™, manufactured by Becton Dickinson). The results are shown in FIG. 3. The numerical value given to each box in the figure indicates the ratio (%) of cells contained in each box.

As shown in FIG. 3, on Day 4 of the culture, there existed B cells that expressed IgG1 and IgE antigen receptors. On Day 10 of the culture, however, almost all of the B cells were confirmed to be of IgG1 type. In addition, almost all of the cells exhibited the phenotypes of germinal center B cells (GL7+, Fas+, CD38low, PNA bound+) (data not shown), with the exception that some cells became CD138-positive (plasma cell lineage).

Example 2

[B] Antibody-Producing Ability of B1-H8 Knock-in Mouse-Derived B Cell Population (1) Preparation of Cells To prepare an NP antigen-specific IgG-positive B cell population, the B cell population of B1-8 heavy chain knock-in mouse was used.

Naive B cells were prepared from the spleen of a B1-8 heavy chain knock-in mouse (Lam K P et al., 1997: Cell 90: 1073) in the same manner as that of Example 1(1). It has been known that B cells exhibiting affinity for a 4-hydroxy-3-nitrophenylacetyl (NP) antigen (λL chain positive) make up approximately 5% of the B cells of the B1-8 heavy chain knock-in mouse.

(2) Confirmation by ELISPOT Method of B Cells that Produce NP Antigen-Recognizing Antibody B1-8 heavy chain knock-in mouse-derived splenic B cells were recovered in the same manner as that of Example 1, κ light chain-negative and NP-binding B cells were recovered using an FITC-anti-mouse κ light chain antibody (manufactured by BD Pharmingen), anti-FITC-microbeads (manufactured by Miltenyi Biotec), NP-BSA-biotin (manufactured by Biosearch Technologies) and avidin-microbeads (manufactured by Miltenyi Biotec), and also using MACS® Separation Columns (manufactured by Miltenyi Biotec). These NP-specific B cells were recovered 4 days after initiation of the culture in the same manner as that of Example 1, and the secondary culture was then initiated. The number of anti-NP IgG1 antibody-producing cells in total B cells was measured on Days 2 and 4 after initiation of the secondary culture by an ELISPOT method. Moreover, the number of IgG1-positive cells was calculated by a flow cytometry in the same manner as that of Example 1. Based on the number of IgG1-positive cells calculated from the results of the flow cytometry, the ratio (%) of anti-NP IgG1 antibody-producing cells was calculated. Specifically, the recovered cells were plated at a cell density of 200 cells/well on NP-CGG-coated MultiScreen (manufactured by MILLIPORE), and they were then culture for 5 hours. Thereafter, the cells were removed by washing, and an anti-mouse IgG1-HRP antibody (manufactured by SouthernBiotech) was reacted therewith. Thereafter, the wells were colored using AEC substrate (manufactured by DAKO), and spots indicating the number of anti-NP IgG1 antibody-producing cells was measured. The results are shown in FIG. 4.

Figure 4:
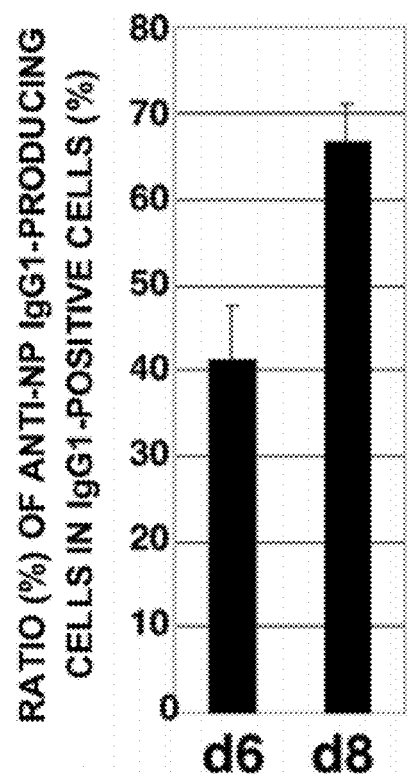
FIG. 4 is a graph showing the ratio of the anti-NP IgG1-producing cells in the cell population of Example 2 of the present invention.

As shown in FIG. 4, it was confirmed that approximately a half of the IgG1-positive B cells, that is 41%±6 on Day 2 after initiation of the secondary culture and 67%±4 on Day 4 after initiation of the secondary culture, were present as anti-NP IgG1 antibody-producing cells. Hence, it was shown that a half of the IgG-positive B cells after the secondary culture step were plasmablasts.

Example 3

[C] Preparation of B1-H8 Knock-in Mouse-Derived IgG-Positive B Cell Population (1) Preparation of Cells In order to confirm that an antigen-specific IgG-positive B cell population could be selected, a B1-H8 heavy chain knock-in mouse-derived B cell population and 40LB-FcY-FL cells were used.

Naive B cells were prepared from the spleen of a B1-8 heavy chain knock-in mouse (Lam K P et al., 1997; Cell 90: 1073) in the same manner as that of Example 1(1).

40LB-FcY-FL cell clones were produced by introducing a mouse Fas-ligand (FL) (Cell, Vol. 75, pp. 1169-1178 (1993)) and a chicken IgY (IgG) receptor (Proc Natl Acad Sci U.S.A., Vol. 104, pp. 11718-11723 (2007)) into 40LB cells according to an ordinary method using a retrovirus vector (Int J. Hematol, Vo. 67, pp. 351-359 (1998)) and then allowing cells to constantly express.

As an antigen that was to be presented to 40LB-FcY-FL cells, an $NP_{42}$-chicken-globulin (CGG) antigen was used (wherein NP was conjugated with CGG according to a common method). The 40LB-FcY-FL cells were plated on a 10-cm plate in the same manner as that of Example 1, and then $NP_{42}$-CGG was put into the plate at 10 µg/ml and reacted for 1 hour at a room temperature, so that it was bound with the 40LB-FcY-FL cells.

(2) Screening for Antigen-Specific IgG-Positive B Cell Population

B1-8 heavy chain knock-in mouse-derived splenic B cells were subjected to a primary culture for 3 days in the same manner as that of Example 1, and were then subjected to a secondary culture for 2 days.

Subsequently, in order to carry out the selective culture of NP antigen-specific B cells, IgE-positive cells and antibody-producing cells were removed from the recovered cultured B cells, using a biotin-anti-mouse IgE antibody (manufactured by BD Pharmingen), a biotin-anti-mouse CD138 antibody (manufactured by BD Pharmingen), and Streptavidin-Particle Plus-DM (manufactured by BD Pharmingen). Thereafter, the remaining cells were cultured together with IL-21 (10 ng/ml, manufactured by PEPRO TECH), using the $NP_{42}$-CGG-bound 40LB-FcY-FL cells. Thirty-six hours later, total cells were recovered, and 40LB-FcYR-FL cells were then removed from the recovered cells, using a biotin-anti-mouse H-2Kd antibody and Streptavidin-Particle Plus-DM (manufactured by BD Pharmingen). Thereafter, the obtained B cells were cultured on new 40LB cells for 3 days in the presence of IL-21 (10 ng/ml, manufactured by PEPRO TECH).

Figure 5:
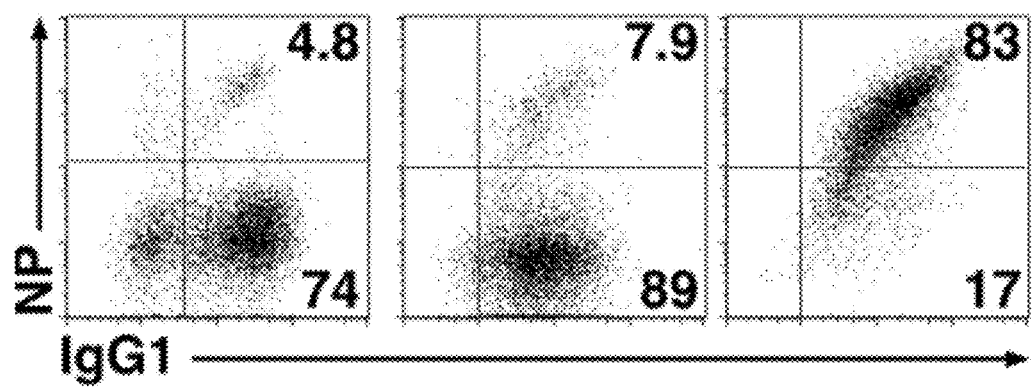
FIG. 5 is a view showing the results of the two-dimensional staining of the cell population obtained after the screening step with NP-conjugated BSA biotin and an anti-IgG1 antibody, performed in Example 3 of the present invention.

After completion of the culture, the cultured cells were recovered, and NP-specific B cells were then detected with the use of a flow cytometer, using NP-BSA-biotin (manufactured by Biosearch Technologies), avidin-PE (manufactured by eBioscience), and an anti-IgG1 antibody (manufactured by SouthernBiotec). The results are shown in FIG. 5. The left view of FIG. 5 shows the cells before selective culture. The right view of FIG. 5 shows the cells obtained by culturing on $NP_{42}$-CGG-bound 40LB-FcYR-FL for 36 hours, recovering the living B cells, and further culturing them in the presence of 40LB and IL-21 for three days. The center view of FIG. 5 shows that the cells were not subjected to selective culture, but were continuously cultured on 40LB, and were then analyzed at the same time of the cells shown in the right view of FIG. 5. The numerical values given to the upper right region and lower right region of FIG. 5 each indicate the ratio (%) of cells contained in each region.

As shown FIG. 5, as a result of the culture of the cells on 40LB-FcYR-FL for 36 hours from d5 to d6.5 (right view of FIG. 5), almost all of B cells that did not bind to NP died, and thus, NP-bound B cells were selected. These results show that antigen-specific B cells were screened for as a result that apoptosis due to Fas receptor stimulation was prevented by antigen receptor stimulation. Accordingly, it was confirmed that the obtained cell population was an NP-specific B cell population comprising NP-specific IgG-positive B cells.

Example 4

[D] Induction of Somatic Hypermutation in GCL-B Cells by Forced Expression of AID B1-8 heavy chain knock-in mouse-derived splenic B cells were subjected to a primary culture in the same manner as that of Example 1. On Day 2 of the culture, AID was forced to be expressed using a retrovirus vector. Specifically, a GFP gene incorporated into a pMX-IRES-GFP retrovirus vector (Proc Natl Acad Sci, U.S.A., Vol. 97, pp. 3062-3066 (2000)) was replaced with human CD8 (hCD8), so as to produce a pMX-IRES-hCD8 retrovirus vector. Mouse AID (J Biol Chem, Vol. 274, pp. 18470-18476 (1999)) was subcloned into the pMX-IRES-hCD8 retrovirus vector according to an ordinary method, so as to produce a pMX-AID-IRES-hCD8 retrovirus vector. The B cells on Day 2 of the culture were infected with the produced pMX-AID-IRES-hCD8 retrovirus vector, and on Day 4 of the culture, the cells were shifted to a secondary culture. After initiation of the culture, antigen receptor stimulation was carried out using an anti-light chain antibody every two days. On Day 9 of the culture, the cells were stained using a biotin-anti-human CD8 antibody (manufactured by Biolegend) and avidin-APC (manufactured by eBioscience), and thereafter, hCD8-positive cells were sorted using FACS VANTAGE™ (manufactured by Becton Dickinson). Using the genomic DNA of the obtained cells, a knock-in heavy chain was amplified by a PCR method using, as templates, the following primers (5'-GGCCGTCGACTGAGCACACAG-GACCTCAC-3': SEQ ID NO: 1) and (5'-CCGGGAATTCT-TCTGACTCCCAAGGTGTCC-3': SEQ ID NO: 2). The amplified fragment was cloned into a plasmid vector, and was then subjected to sequence analysis.

FIG. 6 shows the nucleotide sequence of a B1-8 heavy chain V region (SEQ ID NO: 3, the lower case of FIG. 6) and sequences of mutants each having a mutation in the aforementioned region (the upper and central cases of FIG. 6; this figure shows that the underlined nucleotides are substituted with the nucleotides located above them, and the symbol "-" indicates that the nucleotide located below the symbol is deleted. As a result of the analysis of 24 clones, it was found that a total of 14 nucleotides were substituted or deleted. From these results, the mutation frequency was found to be 0.58 nucleotides per heavy chain. Since it is considered based on the number of cells that approximately 10 times of cell divisions occurred after introduction of AID, the mutation rate can be calculated to be approximately 1/10000/generation.

Accordingly, it was demonstrated that, in the primary culture and the secondary culture of Example 1 and Example 2, a mutation can be introduced into a heavy chain V region at a high frequency by the expression of AID. It is suggested that an antigen-specific B cell population comprising IgG-positive B cells specific to a certain antigen would be obtained by screening for IgG-positive B cells, into the heavy chain V region of each of which a mutation has been introduced at a high frequency, using the certain antigen in the same manner as that of Example 3.

Example 5

[E] Preparation of IgG-Positive B Cell Population Using Human-Derived B Cells

Mononuclear cells were isolated from normal human peripheral blood, using Ficoll (manufactured by GE Healthcare Bio-Sciences), and CD2-negative and CD19-positive B cells were then recovered from the mononuclear cells, using a biotin-anti-human CD2 antibody, an FITC-anti-human CD19 antibody, Streptavidin-Particle Plus DM (manufactured by BD Pharmingen) and anti-FITC microbeads (manufactured by Miltenyi Biotec), and also using MACS® Separation Columns (manufactured by Miltenyi Biotec). The recovered B cells were dispersed on 40LB that had been prepared in the same manner as that of Example 1, and human IL-4 (50 ng/ml, manufactured by PEPRO TECH) and human IL-2 (25 units/ml, manufactured by PEPRO TECH) were added thereto. Thereafter, the obtained mixture was subjected to a primary culture for 4 days. After completion of the primary culture, total cells were recovered in the same manner as that of Example 1. The recovered cells were dispersed on newly prepared 40LB, and human IL-2 (25 units/ml, manufactured by PEPRO TECH) and human IL-21 (10 ng/ml, manufactured by PEPRO TECH) were added thereto. Thereafter, the obtained mixture was subjected to a secondary culture. Three days later, total cells were recovered, and they were continuously cultured for further 3 days under the same conditions as those for the secondary culture.

The number of living cells after completion of the culture was counted in the same manner as that of Example 1, and the increase rate of cells, which were calculated based on the initial number of cells, was obtained. The results are shown in FIG. 7. In FIG. 7, the solid line indicates the number of cells confirmed during the primary culture, and the dotted line indicates the number of cells confirmed during the secondary culture. As a result, it was confirmed that the cells had grown at a factor of approximately 100 for 10 days after initiation of the culture (see FIG. 7).

Figure 8:
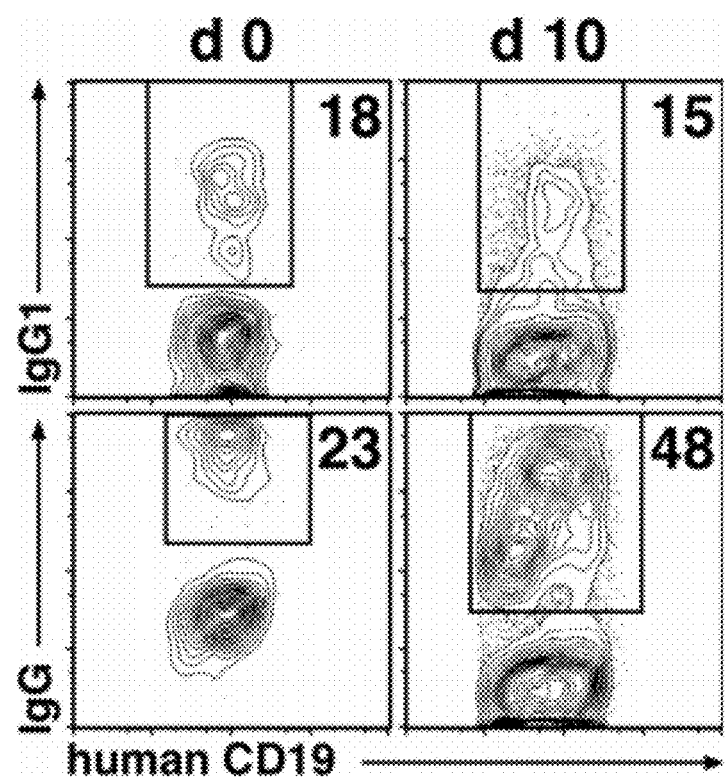
FIG. 8 is a view showing the results of the two-dimensional staining of the cell population of human peripheral blood cells obtained after the secondary culture with an anti-IgG antibody or an anti-IgG1 antibody and an anti-CD19 antibody, performed in Example 5 of the present invention.

Moreover, B cells at the time of initiation of the culture and on Day 10 were stained with an FITC-anti-CD19 antibody (manufactured by eBioscience) and biotin-anti-IgG (manufactured by BD Pharmingen) or a biotin-anti-IgG1 antibody (manufactured by BD Pharmingen), and the cells were then analyzed using a flow cytometer. The results are shown in FIG. 8. The numerical value given to each region enclosed with a box in FIG. 8 indicates the ratio (%) of cells contained in the region.

As shown in FIG. 8, it was confirmed that IgG1-positive cells, which made up 18% in total B cells at the time of initiation of the culture, was decreased to 15%, and that IgG-positive cells, which made up 23% in total B cells at the time of initiation of the culture, was increased to 48%. Accordingly, even in the case of human-derived cell, IgG-positive B cells could be effectively increased by the culture method described in the present Example 1. Therefore, by screening for the obtained IgG-positive B cells using an antigen in the same manner as that of Example 3, an antigen-specific B cell population comprising IgG-positive B cells, which is specific to the aforementioned antigen, can be obtained.

Thus, according to the production method of the present invention, there can be simply obtained a B cell population comprising large quantities of IgG-positive B cells, which exhibits specificity to various types of specific antigens of interest and can produce an antibody against such a specific antigen. Moreover, a high frequency of mutation can be introduced into the V region of this IgG-positive B cell. From these results, it is clear that a cell population of antibody-producing cells, which exhibits specificity to a specific antigen, can be simply produced without the need for carrying out immunization of animals. Since the production method of the present invention does not need the immunization of animals, it can be used to produce an antibody, using a substance having whole body toxicity or a protein having high homology among species as an antigen.

The disclosures of Japanese Patent Application No. 2009-251362 filed on Oct. 30, 2009, are incorporated herein by reference in their entirety.

All publications, patent applications and technical standards cited herein are incorporated herein by reference in their entirety to the same extent as if each individual publication, patent application or technical standard was specifically and individually indicated to be incorporated by reference.

The invention claimed is:

1. A method for producing an antigen-specific B cell population comprising IgG-positive B cells specific to a specific antigen, the method comprising:
   i) culturing IgG-positive B cells together with the specific antigen in the presence of IL-21, CD40L or an antibody that binds CD40, BAFF or an antibody that binds BAFF receptor, and FasL or an antibody that binds Fas; and
   ii) screening for antigen-specific B cells specific to the specific antigen; and
   iii) obtaining an antigen-specific B cell population comprising the IgG-positive B cells specific to the specific antigen.

2. The method according to claim 1, wherein the culturing comprises culturing the IgG-positive B cells together with the specific antigen in the presence of IL-21, CD40L, BAFF and FasL.

3. The method according to claim 1, wherein the IgG-positive B cells are obtained by performing a primary culture of a cell population comprising B cells in the presence of IL-4 and a secondary culture thereof in the presence of IL-21, the primary and secondary culture further comprising culturing the IgG-positive B cells with CD40L or an antibody that binds to CD40, and BAFF or an antibody that binds BAFF receptor.

4. The method according claim 1, wherein the B cells are contacted with a carrier that presents CD40L, BAFF, FasL and the specific antigen.

5. The method according to claim 4, wherein the carrier is a feeder cell that presents CD40L, BAFF, FasL and the specific antigen.

6. A method for producing a monoclonal antibody, comprising:
   i) culturing IgG-positive B cells together with a specific antigen in the presence of IL-21, CD40L or an antibody that binds CD40, BAFF or an antibody that binds BAFF receptor, and FasL or an antibody that binds Fas;
   ii) screening for antigen-specific B cells specific to the specific antigen and obtaining an antigen-specific B cell population comprising the IgG-positive B cells specific to the specific antigen;
   iii) fusing myeloma cells with the antigen-specific B cell population and obtaining hybridomas;
   iv) isolating a hybridoma that produces an antigen-specific antibody specific to the specific antigen from the hybridomas; and
   v) recovering the antigen-specific antibody produced by the hybridoma that produces the antigen-specific antibody.

* * * * *

SEQUENCE LISTING

```
<160> NUMBER OF SEQ ID NOS: 3

<210> SEQ ID NO 1
<211> LENGTH: 29
<212> TYPE: DNA
<213> ORGANISM: Artificial
<220> FEATURE:
<223> OTHER INFORMATION: primer(1) Hv

<400> SEQUENCE: 1
ggccgtcgac tgagcacaca ggacctcac                                    29

<210> SEQ ID NO 2
<211> LENGTH: 30
<212> TYPE: DNA
<213> ORGANISM: Artificial
<220> FEATURE:
<223> OTHER INFORMATION: prier(2) Hv

<400> SEQUENCE: 2
ccgggaattc ttctgactcc caaggtgtcc                                   30

<210> SEQ ID NO 3
<211> LENGTH: 499
<212> TYPE: DNA
<213> ORGANISM: Mus musculus
```

```
<400> SEQUENCE: 3
atgggatgga gctgtatcat cctcttcttg gtagcaacag ctacaggtaa ggggctcaca        60
gtagcaggct tgaggtctgg acatatatat gggtgacaat gacatccact ttgcctttct       120
ctccacaggt gtccactccc aggtccaact gcagcagcct ggggctgagc ttgtgaagcc       180
tggggcttca gtgaagctgt cctgcaaggc ttctggctac accttcacca gctactggat       240
gcactgggtg aagcagaggc ctggacgagg ccttgagtgg attggaagga ttgatcctaa       300
tagtggtggt actaagtaca atgagaagtt caagagcaag gccacactga ctgtagacaa       360
accctccagc acagcctaca tgcagctcag cagcctgaca tctgaggact ctgcggtcta       420
ttattgcgca agatacgatt actacggtag tagctacttt gactactggg gccaaggcac       480
cactctcaca gtctcctca                                                   499
```